United States Patent [19]

Puumalainen

[11] Patent Number: 5,543,331
[45] Date of Patent: Aug. 6, 1996

[54] METHOD OF DETECTION OF ALIEN MATTER CONTENTS IN GASES

[75] Inventor: Pertti Puumalainen, Savonlinna, Finland

[73] Assignee: Fabretti Holdings Limited, Gibraltar, Finland

[21] Appl. No.: 342,007

[22] Filed: Nov. 16, 1994

Related U.S. Application Data

[63] Continuation of Ser. No. 39,112, filed as PCT/FI91/00316, Oct. 10, 1991 published as WO92/07255, Apr. 30, 1992, abandoned.

[30] Foreign Application Priority Data

Oct. 11, 1990 [FI] Finland ................................ 904997

[51] Int. Cl.$^6$ ....................................................... G01N 21/71
[52] U.S. Cl. .................. 436/153; 73/31.02; 73/31.03; 73/31.05; 250/382; 250/385.1; 250/387; 324/464; 324/469
[58] Field of Search ................................ 436/153; 422/90; 73/31.02, 31.03, 31.05; 324/464, 469; 250/381, 382, 385.1, 387

[56] References Cited

U.S. PATENT DOCUMENTS 2,422,264  6/1947  Seaman ................................ 250/281
4,445,038  4/1984  Spangler et al. ................... 250/382
5,047,723  9/1991  Puumalainen ..................... 324/464
5,227,628  7/1993  Turner ................................ 250/286

FOREIGN PATENT DOCUMENTS 0027748  4/1981  European Pat. Off. ....... G01N 27/66
8707720  12/1987  European Pat. Off. ....... G01N 27/62
9009583  8/1990  European Pat. Off. ....... G01N 27/64
75055  4/1988  Finland ......................... G01N 27/62

Primary Examiner—David A. Redding
Attorney, Agent, or Firm—Cushman Darby & Cushman

[57] ABSTRACT

The objective of the invention is a method for detection of alien matter contents in gas, in which method the gas and the substances contained in it are ionized in an ionization room (1). By the present methods impurities in gases cannot be determined fast and in small concentrations. In the method of the invention the ions contained in the gas are separated in a separation section (2) into positive and negative ions, of which at least the ions of either sign are led into a narrow analyzer channel (4). There, due to the capillary force, they are forced to move in the middle section of the channel, from where they are deflected by electric fields of different strength caused by different voltages (U1–U10) into an electrode located at the edge of the channel, where they cause ion current (I1–I10). On the basis of ion currents a current spectrum is made, on the basis of which different substances are detected and their concentrations determined with the aid of corresponding spectra obtained with standard samples of different substances.

5 Claims, 1 Drawing Sheet

METHOD OF DETECTION OF ALIEN MATTER CONTENTS IN GASES

This is a continuation of application Ser. No. 08/39,112, filed as PCT/FI91/00316, Oct. 10, 1991 published as WO92/07255, Apr. 30, 1992, which was abandoned upon the filing hereof.

The object of the invention is a method for detection of alien matter contents in gases, in which method the gas is first ionized and alien matters are detected and determined by the behaviour of formed ions.

Alien matter contents are often detected and determined in order to control that the air is safe to breath. Particularly, when analyzing certain very poisonous substances, which appear in small quantities, other substances of air may disturb detection. The quantities of different substancies, such as carbon dioxide, may vary in air. The detection of different molecules or molecule groups from gases or vapour of vaporized solid or liquid materials is often connected with problems. Particularly, detection of poisonous substances, such as nerve gases spread in the air, reliably and fast enough from small quantities, is difficult. The detection should be made in a few seconds and, with the most effective nerve gases, from concentrations as small as 1/100 ppm.

At present the most sensitive analyzing devices are based on ionizing the air for example by alfa or beta radiation and measuring the ions in different circumstances. In one method, the ions are made to penetrate through a certain kind of a labyrinth and the remaining ions are measured from the current they generate. Another method observes the mobility of the ions through different grids and finally ion current is measured. By these two methods very heavy molecules, such as most combat gases, can be detected from air. In one method ionized molecules are led through chambers, which have different electric fields, and the nature and concentration of the molecules of alien matters are tried to be detected by measuring the current from these electric fields. This method is rather efficient, but the recombination of different charges is a problem, because it makes ions disappear faster.

The air of the invention is to bring about a method for the detection of alien matter contents in gases, by which the nature and quantity of different alien matter components in a gaseous state are measured and detected, even small concentrations, such as below 1 ppm. In particular the purposes of the invention is to bring forth a method, by which the consistency and quantity of nerve gases or other similar gases can be detected quickly and early.

The aim of the invention is achieved by a method, the characteristics of which are presented in the claims.

In the method according to the invention the gas and the different substances contained in it are ionized in a ionization room by applicable radiation, for instance by alfa radiation. After this the gas is transferred into a separating part, where the ions in the gas are separated into positive and negative ions. At least the ions with one sign are led into a narrow analyzing channel, in which they are forced to move in the middle section of the channel because of the capillary force. From here they are taken by electric fields of different strength to an electrode located at the edge of the channel, where they cause ion current. On the ground of the ion currents a current spectrum is calculated, from which different substances are detected and their concentrations determined with the aid of corresponding spectra calculated from standard samples of different substances. The analyzing channels are made narrow, so the ions move in them without losses, even distances of several tons of meters, especially when they are well separated from the ions with opposite sign. This is the so called capillary transportation, which is known from some ion transportation equipments used in nuclear physics. In the capillary space the ions are deflected with different electric fields away from the carrier gas, small and highly charged ions or particles are deflected by a low voltage, while large molecules or particles with a small charge require a high voltage. When this is done in both channels, we get a spectrum, in which for example x-axis is the voltage from negative (deflection of positive ions) to positive (deflection of negative ions), and y-axis is the ion current measured from corresponding deflection spot. From this spectrum different substances can then be detected based on the spectra of standard samples.

The method is functioning in atmospheric pressure or in underpressure. The air can be filtered mechanically before the analysis or, for example moisture can be removed. Often the air is also heated in order to vaporize the aerosol particles contained in it. If liquids are analyzed, they are first brought into a gaseous state by lowering the pressure and/or heating.

In a favourable embodiment of the invention positive ions are deflected to one edge and negative ions to the other edge of the separation section by a magnetic field perpendicular to the direction of the gas flow. Also, absorption of the ions, which have been forced to the edge of the channel in the separation section, is prevented by charging the wall with a charge whose sign is equal to the charge of the ion. In another favourable embodiment of the invention the ions are separated into positive and negative by an electric field across the separation section, in which case the positive ions go towards one edge and the negative ions towards the other edge. In some embodiments one or more electric fields can be used and/or electric and magnetic fields at the same time.

In one favourable embodiment successive grids are placed into the channels, which are branched off from the channel that goes through the separation section, and the voltage in these grids increases form one grid to the next in positive direction in a channel for negative ions and in negative direction in a channel for positive ions. This way the flow is made more effective.

BRIEF DESCRIPTION OF DRAWINGS

In the following the invention is explained more in detail by referring to the attached drawing, in which.

Figure 1A:
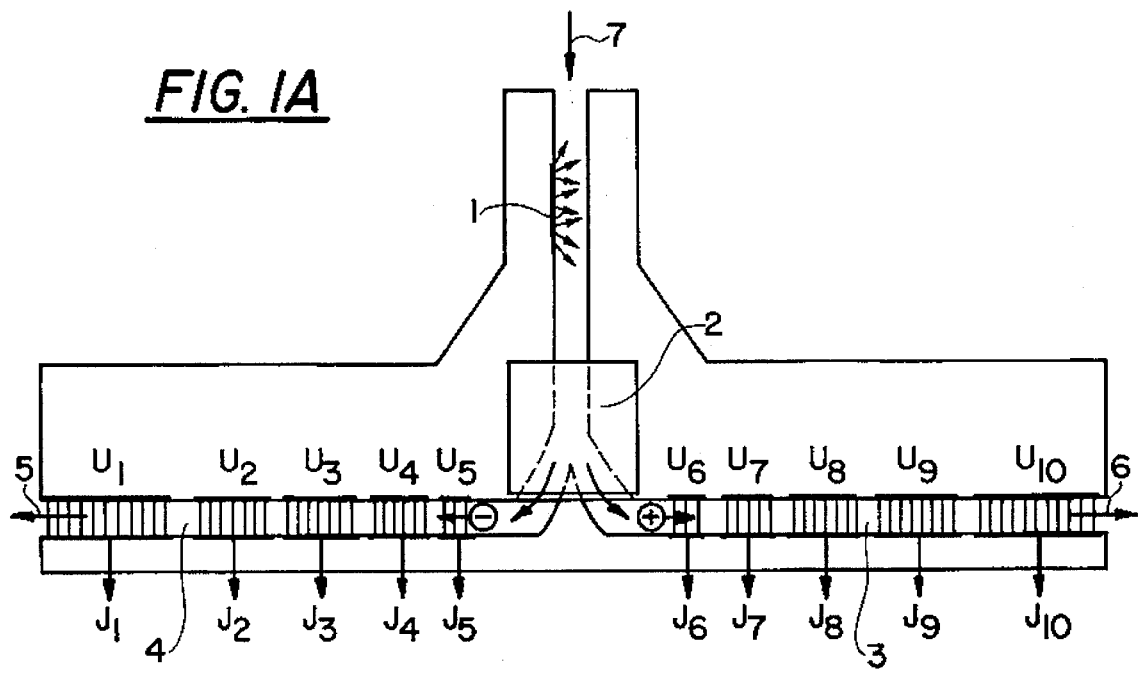
FIG. 1A presents a device system for the application of the method in accordance with the invention in cross-section and seen from the side.

In the embodiment presented in FIG. 1A the gas 7, which is led into the device system, is continuously ionized in the chamber 1 by an alfa radiation source. After this the gas is led into the separation section 2, where it is separated by one or more electric fields or by electric and magnetic fields together so that the negative ions in this embodiment are taken to the left and the positive ions are taken to the right into the analyzing channels 3 and 4. In the analyzing channels the ions are deflected by different electric fields, caused by voltages $U_1$–$U_5$ in the channels for negative ions, and we can measure positive ion currents $I_1$–$I_5$. In the analyzing channels for positive ions, ions are deflected by electric fields caused by voltages $U_6$–$U_{10}$, and we can measure ion currents $I_6$–$I_{10}$. The voltages in the channels can vary as wanted, and also the lengths of the electric fields. The height of the channel must, however, by such, that the so called capillary forces have a strong effect on the ions, that is the ions tend to move along the center of the channel. In other words, the height of the channel is preferably less than 1 mm. From the analyzing channels the gas is sucked through the air pumps 5 and 6 away from the device system.

Figure 1B:
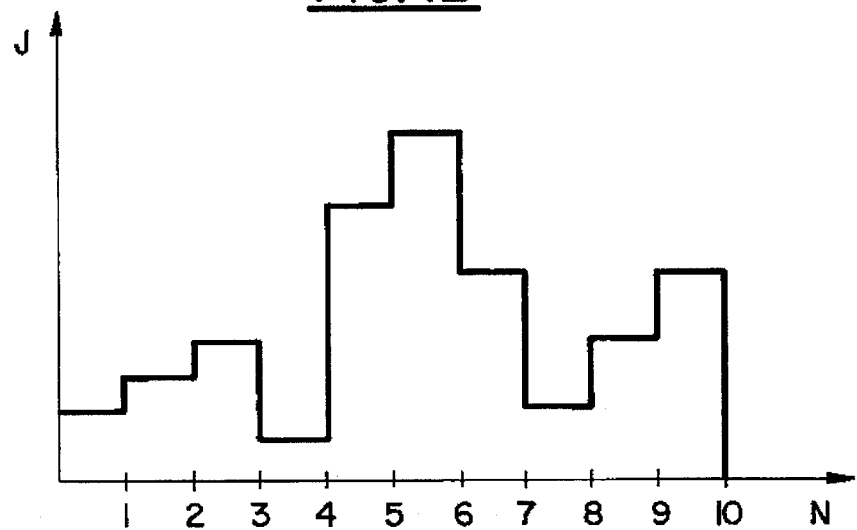
FIG. 1B presents a current spectrum obtained by a device system presented in FIG. 1A.

FIG. 1B presents a current spectrum obtained from measurements. In principle, a different spectrum is always obtained with different molecules. On the basis of the current spectrum, different substances are recognized and their concentrations in the gas are determined. In this the corresponding spectra obtained by measurements with standard samples of different substances are used. If the strengths of the fields are appropriately changed, differencies between differing molecule groups can be emphasized and for example different nerve gases can be detected.

The invention is not limited to the presented example of usage, but it can further more be used in many other embodiments besides analyzing of air. Such embodiments are for example monitoring of industrial processes, where different molecules are recognized in the detectors of different chromatographs, such as liquid and gas chromatographs. The amount and values of the electric fields, and also the geometry of the device, can be varied unlimitedly. For the positive and/or negative ions two or more analyzing channels can be used, in which case also the ratios between the current caused by ions deflected in different electric fields are measured. The separator section can also be different, the main thing is, that it separates the ions for the most part into positive and negative.

I claim:

1. A method of determining alien matter content in a gas using a device having a separation section and analyzing channels, the method including:

ionizing the gas and the alien matter contained therein, separating the ions into positive and negative ions in the separation section, directing positive ions to one analyzing channel and negative ions to another analyzing channel, using gaseous capillary transport force to move the ions generally along a center portion of a respective channel, using electric fields of different strengths to deflect the ions in their respective channels toward an electrode disposed at the end of each channel, measuring positive and negative ion currents, developing a current spectrum based on said ion currents on the basis of which different alien matter is recognized, and determining concentrations of the alien matter by using corresponding spectra obtained with standard samples of different alien matter.

2. The method according to claim 1, wherein the step of separating the ions includes deflecting positive ions to one wall of the separation section and deflecting the negative ions to another wall of the separation section by a magnetic field acting perpendicular to a direction of gas flow into the separation section.

3. The method according to claim 2, further including preventing absorption of ions by charging each of the walls of the separation section with the same polarity as the ion being separated at a respective wall.

4. The method according to claim 1, including placing successive grids into the analyzing channels in such a manner that voltage rises to a positive direction in the channel for the negative ions and the voltage rises to a negative direction in the channel for the positive ions when moving from one grid to the next grid.

5. The method according to claim 1, wherein the ions are separated into positive and negative ions by a cross-wise electric field, such that the positive ions move towards one wall of the separation section and the negative ions move towards another wall of the separation section.

\* \* \* \* \*